United States Patent
Carlén et al.

(10) Patent No.: US 8,157,776 B2
(45) Date of Patent: Apr. 17, 2012

(54) METHOD AND ARRANGEMENT FOR DETECTION OF A SYNCHRONIZING MARK BEING USED IN SYNCHRONIZED POSITIONING OF AT LEAST ONE ESSENTIALLY CONTINUOUS MATERIAL WEB

(75) Inventors: Henrik Carlén, Västra Frölunda (SE); Ralph Dovertie, Västra Frölunda (SE); Anders Norder, Lindome (SE)

(73) Assignee: SCA Hygiene Products AB, Göteborg (SE)

( * ) Notice: Subject to any disclaimer, the term of this patent is extended or adjusted under 35 U.S.C. 154(b) by 528 days.

(21) Appl. No.: 12/297,704

(22) PCT Filed: Apr. 27, 2006

(86) PCT No.: PCT/SE2006/000518
§ 371 (c)(1),
(2), (4) Date: Oct. 20, 2008

(87) PCT Pub. No.: WO2007/126347
PCT Pub. Date: Nov. 8, 2007

(65) Prior Publication Data
US 2009/0082747 A1    Mar. 26, 2009

(51) Int. Cl.
*A61F 13/15* (2006.01)
*B29C 65/00* (2006.01)
(52) U.S. Cl. ............... 604/385.01; 156/64; 156/229
(58) Field of Classification Search .......... 604/385.01; 156/64, 229
See application file for complete search history.

(56) References Cited

U.S. PATENT DOCUMENTS

| | | | |
|---|---|---|---|
| 5,235,515 | A | 8/1993 | Ungpiyakul et al. |
| 5,766,389 | A | 6/1998 | Brandon et al. |
| 6,354,984 | B1 | 3/2002 | Hensley et al. |
| 6,764,563 | B2 | 7/2004 | Henry et al. |
| 6,955,733 | B2 | 10/2005 | Miller et al. |
| 2003/0105443 | A1 | 6/2003 | Ohnishi |
| 2003/0136495 | A1 | 7/2003 | Miller et al. |

(Continued)

FOREIGN PATENT DOCUMENTS
WO    WO 99/32384 A1    7/1999
(Continued)

OTHER PUBLICATIONS

International Search Report for corresponding application PCT/SE2006/000518, completed Nov. 27, 2006.

(Continued)

*Primary Examiner* — Jacqueline F. Stephens
(74) *Attorney, Agent, or Firm* — Buchanan Ingersoll & Rooney PC

(57) ABSTRACT

A method for detection of a synchronizing mark (6) being used in synchronized positioning of at least one essentially continuous material web (2), for manufacturing products (20) that have printed motifs (5; 5') or similar processed elements, which material web (2) is intended to be divided into a nominal division length ($L_N$) and has synchronizing marks (6) with a periodicity ($L_S$), which method includes: detection of the respective synchronizing mark (6) for positioning the respective motif (5; 5') in a predetermined position on the respective product (20), which detection is carried out along a predetermined in the machine direction longitudinal section (24) of the material web (2), and detection of the synchronizing mark (6) by distinguishing its color or color combination from colors or color combinations in the rest of said section (24). An arrangement for such detection, and an absorbent product.

15 Claims, 3 Drawing Sheets

U.S. PATENT DOCUMENTS

2005/0125180 A1  6/2005  Miller et al.

FOREIGN PATENT DOCUMENTS

| WO | WO 00/59429 | A1 | 10/2000 |
| WO | WO 01/56525 | A1 | 8/2001 |

OTHER PUBLICATIONS

Written Opinion of the International Searching Authority for corresponding application PCT/SE2006/000518.

Extended European Search Report issued on May 26, 2011 in corresponding EP 06733373.2.

METHOD AND ARRANGEMENT FOR DETECTION OF A SYNCHRONIZING MARK BEING USED IN SYNCHRONIZED POSITIONING OF AT LEAST ONE ESSENTIALLY CONTINUOUS MATERIAL WEB

TECHNICAL FIELD

The present disclosure relates to a method for detection of a synchronizing mark that is used for synchronized positioning of at least one essentially continuous material web, for manufacturing products that comprise printed motifs or similar processed elements.

The disclosure also relates to an arrangement for detecting a synchronizing mark that is utilized for synchronized positioning of at least one essentially continuous material web for manufacturing products that comprise printed motifs or similar processed elements.

The disclosure also relates to an absorbent product such as a diaper, incontinence protector, sanitary towel or panty liner, with a predetermined division length and comprising a backing material that has a processed element in a predetermined position in the form of a printed motif or similar processed element, and comprising a synchronizing mark that recurs with a periodicity, with said synchronizing mark being arranged in a predetermined longitudinal section of said backing material.

BACKGROUND ART

A manufacturing process for the production of absorbent products such as diapers, incontinence protectors, sanitary towels and panty liners normally comprises a processing of various continuous material webs, which are fed out from rolls or the like and passed through various work stations for the carrying out of various work elements and process steps. For example, it is common for a manufacturing process for absorbent products to provide a first material web that defines a backing layer consisting of a plastic film that is non-permeable to liquid and a second material web that defines an outer layer consisting of a liquid-permeable material, for example a non-woven material. The product can also be provided with other components, such as for example an absorbent core of a material intended to absorb bodily fluids.

The work elements that are carried out during a process of the type described above can consist, for example, of attaching together two or more layers of material, perforating, cutting, gluing, embossing a pattern or other type of shaping and processing of the materials involved. Other examples of work elements are the application of different components, such as fastening devices (so called tabs), cellulose centres, elastic material, so-called disposal tapes, etc.

In all, the material webs in question go through various process steps that result in a continuous complete material web that consists of a continuous row or strip of a number of absorbent products. Each individual product is finally shaped by this web being cut at regular intervals that correspond to the length of the finished product.

In a process of the type described above, some form of decorative element is often applied, such as a printed pattern or pictures, which are intended to enhance the visual impression of the finished product. Such a printing process is preferably carried out by conventional multi-colour printing. In particular, concerning absorbent products in the form of diapers for babies, such printed motifs, for example in the form of fairy-tale characters and cartoon characters, are considered to make the product more appealing to the consumer. In addition, such a procedure for printing a motif is suitably carried out on the backing layer for a diaper, not least due to the fact that such a backing layer is normally made of a polymer film that is essentially non-permeable to liquid, the surface of which is suitable for colour printing with a good quality and high resolution. In this way, a printed back is obtained on the finished product.

Certain types of printed motif are of such a nature that they can be positioned and oriented in any way on the back of the product. Such a printed motif can then be said to be "unsynchronized" in the sense that it does not need to be positioned in a given and precise way along the back of each product. This can, for example, be the case with an irregular pattern or a motif in the form of abstract symbols, the location of which on the back does not need to have a particular geometrical positioning on the product concerned.

There are, however, other types of printed motifs that can be said to be "synchronized" in the sense that they must be placed in a given position on the layer in question so that each individual product is provided with a print that is always in a predetermined position. An example of such a synchronized print can be a motif that is intended to be printed in the middle of the back of the product, that is centred both longitudinally and laterally.

Against the background of the above, it has been found that there is a need for simple, reliable and cost-effective methods and arrangements that have a high level of precision and using which a synchronized print in the form of patterns, characters and other motifs can be provided on an absorbent article. More specifically, the material web that carries the print in question is to be synchronized in an arrangement for manufacturing the product in question, so that the various work elements that are carried out on the product are carried out in the correct positions in relation to the printed motif.

A previously known way of obtaining such a synchronized printing process is to utilize previously printed reference marks or synchronizing marks that are suitably positioned at regular intervals on the material web in question. Each synchronizing mark can be printed as a small strip of colour along the edge of the material web and can be detected electronically by means of an optical detector. Such synchronizing marks are then used to control the manufacturing process for the product concerned so that, in its final position, the motif that is to appear on the finished product is always in the intended position on the finished product.

It can be noted that the known technology is based on a synchronizing mark having to be positioned well separated from the actual motif, so that the detecting device that is used to detect the synchronizing mark is not also triggered by the motif that is printed on the product in question. This limits the available area within which a printed motif can be applied, which is of course a disadvantage associated with the known technology.

Patent document WO 00/59429 shows an arrangement that utilizes synchronizing marks for controlling the positioning of a printed motif on an absorbent product. According to this document, synchronizing marks are provided on such sections of the product that are cut away later during the manufacturing process. In this way, temporary synchronizing marks are defined that are removed before the product has been completed.

In addition, document WO 99/32384 shows an arrangement for synchronizing two material webs during the manufacture of absorbent products. One of these material webs consists of a backing layer that comprises printed motifs, which are then to be synchronized with an additional material web that comprises an outer layer and an absorbent core. According to WO 99/32384, a stretching of the backing layer is obtained when required, with the object of synchronizing the two material webs.

Against the background of the abovementioned known technology, it can be pointed out that there is a need for methods and arrangements for improved synchronization of printed motifs and similar elements on absorbent products of various kinds, in particular for a precise detection of a synchronizing mark that is used in such a process for synchronization. For example, there is a desire to utilize an ever-increasing part of the material web concerned for printing various types of motif. This desire is in contrast to the requirement for a reliable detection of a synchronizing mark by positioning it a relatively short distance away from the printed motif on the absorbent product, as otherwise too large a motif could be interpreted as a synchronizing mark during the actual detection of the latter.

OBJECT AND SUMMARY

An object of the present is thus to provide an improved method and arrangement for synchronized positioning of motifs, by accurate detection of a synchronizing mark, which method and arrangement can be used when manufacturing products, taking a continuous material web as a starting point.

The above object is achieved by a method of the type described in the introduction, which method comprises: detection of said synchronizing mark by distinguishing its colour or colour combination from colours or colour combinations in a remainder of said section.

The object is also achieved by an arrangement of the type described in the introduction, which arrangement is characterized in that the control unit is arranged to detect said synchronizing mark by distinguishing its colour or colour combination from colours or colour combinations in the remainder of said section.

The object is also achieved by an absorbent product of the type mentioned in the introduction, which is characterized in that said synchronizing mark is arranged with a colour or colour combination that can be distinguished from colours or colour combinations in the remainder of said section.

Important benefits are obtained by means of the invention. In particular, it can be pointed out that the disclosure makes it possible to utilize a larger part of the surface of the article for printing different motifs, in comparison with known technology. This is mainly due to the fact that the synchronizing mark is given a colour or colour combination that does not occur elsewhere in said section. In addition, a more reliable detection of a synchronizing mark by making the detection process clearer and simpler, which is important, not least at the high process speeds associated with the manufacture of absorbent products.

DETAILED DESCRIPTION OF THE PREFERRED EMBODIMENTS

The invention will be described in the following in association with preferred embodiments and the attached drawings, in which.

MODES FOR CARRYING OUT THE INVENTION

Figure 1:
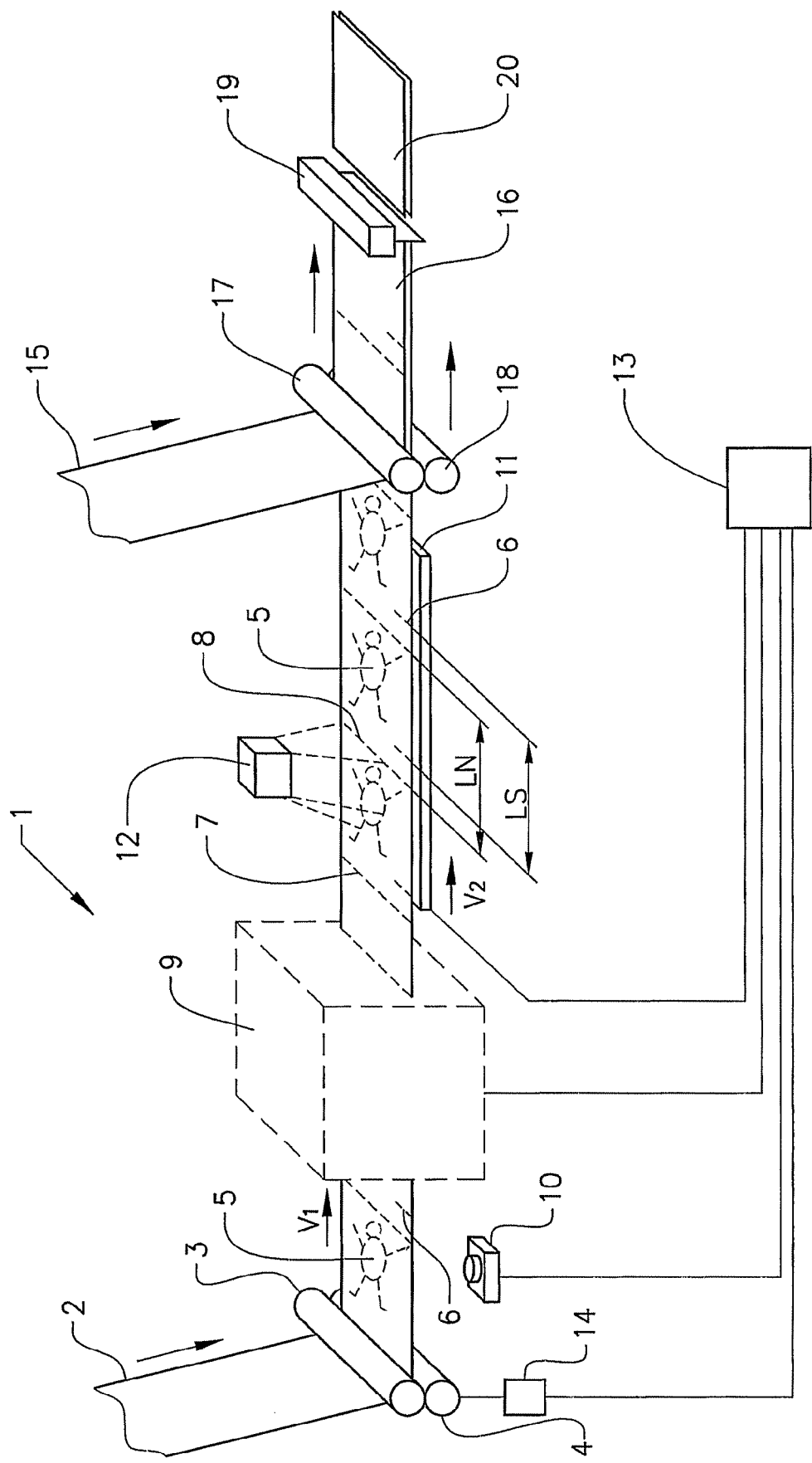
FIG. 1 is a schematic view of an arrangement arranged in accordance with a preferred embodiment of the present invention.

FIG. 1 is a schematic and simplified view of an arrangement 1 for manufacturing absorbent products, which is arranged in accordance with a preferred embodiment of the present invention. More specifically, the arrangement 1 is arranged for manufacturing absorbent products that start out as a first essentially continuous material web 2, which is fed forward in a known way from a roll (not shown) or the like, in a direction that is indicated by an arrow in FIG. 1.

According to the preferred embodiment, the first material web 2 consists of a backing layer for a disposable diaper, that is a material of the type that is non-permeable to liquid or that has at least a high resistance to the penetration of liquid, but which, however, is breathable. For this purpose, the first material web 2 consists suitably of a thin and waterproof plastic film of, for example, polyethylene, polypropylene or polyester. Alternatively, a laminate of non-woven material and plastic film or other suitable and previously-known layers of material can be utilized as a liquid-tight backing layer.

The first material web 2 can be fed forward by means of two rollers 3, 4 which are arranged to give the first material web 2 that will become the backing layer, a certain given feed speed $v_1$.

FIG. 1 also shows that the first material web 2 is processed in such a way that it comprises a printed motif 5. This motif 5 is suitably pre-printed on the first material web 2. In addition, the motif 5 is applied in a periodic way with a certain given interval, so that one and the same motif is provided on each individual product that is manufactured from the first material web 2. In addition, the motif 5 is indicated by broken lines in FIG. 1 to indicate that it is printed on the underside of the first material web 2. In the finished product, the final position of the printed motif 5 will thus be in a predetermined position on the back of the product.

The motif 5 is printed with certain given periodicity and is intended to be synchronized, which means that the final position of the motif 5 is intended to be in the same position on each individually manufactured product of the type in question. For this purpose, the first material web 2 is provided with a number of reference marks or synchronizing marks 6, suitably in the form of relatively short lines that are suitably pre-printed onto the first material web 2. In the embodiment shown in FIG. 1, the synchronizing marks 6 are printed on the underside of the first material web 2. The invention is not, however, restricted to this, it being possible to print the synchronizing marks 6 on both sides of the first material web 2.

In FIG. 1, the synchronizing marks 6 are also indicated by broken lines, in order to indicate that they are printed on the underside of the first material web 2. As will be described in detail below, the object of the respective synchronizing mark 6 is to constitute a detectable reference element, by means of which various work elements and process steps that are carried out by means of the arrangement 1 are synchronized correctly in relation to the respective printed motif 5. In this way, the motif 5 can be positioned in the correct position on the finished product.

In the embodiment that is shown in FIG. 1, a processed element in the first material web 2 is utilized, in the form of a printed motif 5. It should, however, be noted that the principle behind the invention is not limited to only the case when a printed motif is utilized. In other words, the invention can also be used for other positioned elements in the form of patterns, embossing, applications and ornamentation that constitute processing of the first material web 2. Similarly, the principle behind the invention can be used for elements that consist of embossed patterns, folds, notches, holes and similar elements that are intended to be positioned in a predetermined, that is "synchronized", way on a finished product.

As shown in FIG. 1, the first material web 2 can be divided into a certain nominal division length $L_N$, that is a length that is defined between two transverse positions 7, 8 that delimit a particular product. According to the embodiment that is shown in FIG. 1, the nominal division length $L_N$ consists in particular of a product length that corresponds to the front edge and back edge of a finished product. These positions 7, 8 are indicated by broken lines in FIG. 1. However, these lines are not printed on the first material web 2.

Each printed motif 5 is placed in a position that is in a given and predetermined relationship to the respective synchronizing mark 6. This means that the respective synchronizing mark 6 is printed a periodically recurring distance apart $L_S$ that corresponds to the periodicity of the printed motif 5.

As shown in FIG. 1 in a schematic and simplified way, the first material web 2 is fed through a processing equipment 9 where a number of work elements and process steps are carried out in a way that is already known. These work elements can comprise, for example, the application of various types of absorbent material, wadding material and the like, and any other material and components such as, for example, elastic, adhesive tape and the like. The work elements that are carried out in the processing equipment 9 can also comprise folding, cutting, ultrasound welding and other processing steps. The manufacture of absorbent products by means of a series of such work elements is already known, and for this reason will not be described here in detail. As an example, however, reference can be made to said patent document WO 00/59429 mentioned in the introduction, that describes an example of a previously-known manufacturing process for absorbent products.

Still with reference to FIG. 1, it can be noted that the first material web 2 has passed a detecting device 10 just before it is fed into the processing equipment 9. In a way that will be described in detail below, the detecting device 10 is arranged to detect the position of each synchronizing mark 6. The feeding of the first material web 2 is carried out by means of a feeding device that preferably consists of a suction conveyor 11 which is a known feeding device that can be controlled to feed forward the first material web 2 at a given feed speed $v_2$. In addition, the first material web 2 is fed past a gluing station 12 at which adhesive is applied in order to enable a subsequent outer layer to be glued on, in the way that will be described below.

The detecting device 10 consists preferably of a suitable device for optical inspection, according to the embodiment in the form of a video camera that is arranged in association with the first material web 2. The detecting device 10 is arranged in such a way that it continually inspects and records images along the underside of the first material web 2 as shown schematically in FIG. 2. For this purpose, the detecting device 10 comprises a set of light-sensitive elements, by means of which it records the light transmission from the first material web 2 while this is moved in relation to the detecting device 10.

In addition, the detecting device 10 is connected to a computer-based control unit 13. Information from the detecting device 10 is transmitted in this way to the control unit 13, which in turn is provided with software for image processing that is arranged to detect each synchronizing mark 6 that passes over the detecting device 10. In addition, the control unit 13 is connected, in a way that will be described in detail below, to a speed-regulating device 14 for controlling the speed $v_1$ at which the first material web 2 is fed forward. The control unit 13 is also connected to the suction conveyor 11 for regulating the speed $v_2$ of this.

According to an alternative embodiment, the detecting device 10 can be, for example, a CCD camera ("charged coupled device"), that is with a set of light-sensitive sensors arranged in one or more rows. By means of this arrangement, the position of each synchronizing mark 6 can be detected. According to yet another alternative embodiment, the detecting device can be based on, for example, laser technology, that is with a laser light source that is utilized in conjunction with a light-sensitive detector to detect the position of the respective synchronizing mark 6. According to yet another variant, the synchronizing mark can consist of an electronically detectable sensor, for example of the transponder type, that is applied on the first material web 2 with the abovementioned periodicity $L_s$. Such a synchronizing mark can then be read by a detecting device that comprises a radio transmitter and radio receiver for this purpose in a known way. According to yet another alternative embodiment, said synchronizing marks can be printed with magnetic ink that can then be detected by a sensor that detects magnetism.

When the first material web 2 has been fed past the detecting device 10, it meets a second material web 15, according to the embodiment in the form of an essentially liquid-permeable layer that is intended to form an outer layer of the finished product. For this reason, the second material web 15 consists suitably of a non-woven material with a soft and smooth surface, such as, for example, a spun bond material of polypropylene fibre. Other examples of materials that are suitable for constituting the outer layer are perforated plastic films, such as, for example, a perforated polyester film.

The second material web 15 is thus joined to the first material web 2 (together with any additional layers of material and other components that are added in association with the processing equipment 9 as described above) for example by means of the adhesive that was previously applied at the gluing station 12. In this way, a complete material web 16 is created, intended to define a number of manufactured products, which is fed forward in a direction that is indicated by an arrow in FIG. 1 and taken up and fed forward by means of two additional driving units, for example in the form of two rotating feeding rollers 17, 18 arranged respectively over and under the complete material web 16. In this way, the complete material web 16 can be fed forward.

After the assembly with the second material web 15, a complete continuous material web 16 is thus created, consisting of a number of finished absorbent products that are still joined together. This material web 16 is finally fed past a cutting station 19, suitably of the "cross-cutter" type, where cutting is carried out at positions that essentially correspond to the imaginary boundary lines 7, 8 for each finished product. In this way, a number of finished products are created in the form of absorbent products 20.

With reference again to the detecting device 10, it can be noted in particular that this is arranged to detect the position of the respective synchronizing mark 6. Information regarding a detected position for a given synchronizing mark 6 is then used for various process steps that, for example, are carried out in the processing equipment 9 in order to ensure that the printed motif 5 is always positioned in a correct position on each finished product 20.

The detection of the respective synchronizing mark 6 will now be described in greater detail with reference to FIG. 2, which shows a view from above of a part of the first material web 2 that is fed forward in a direction that is indicated by an arrow. The first material web 2 can be said to be divided into a number of products 20 that are delimited by means of imaginary lines 7, 8. In this way, a nominal division length $L_N$ is defined for each product 20, as described above. The material web 2 is also provided with a printed motif 5 intended to be positioned in a predetermined way on the respective product 20.

Figure 2:
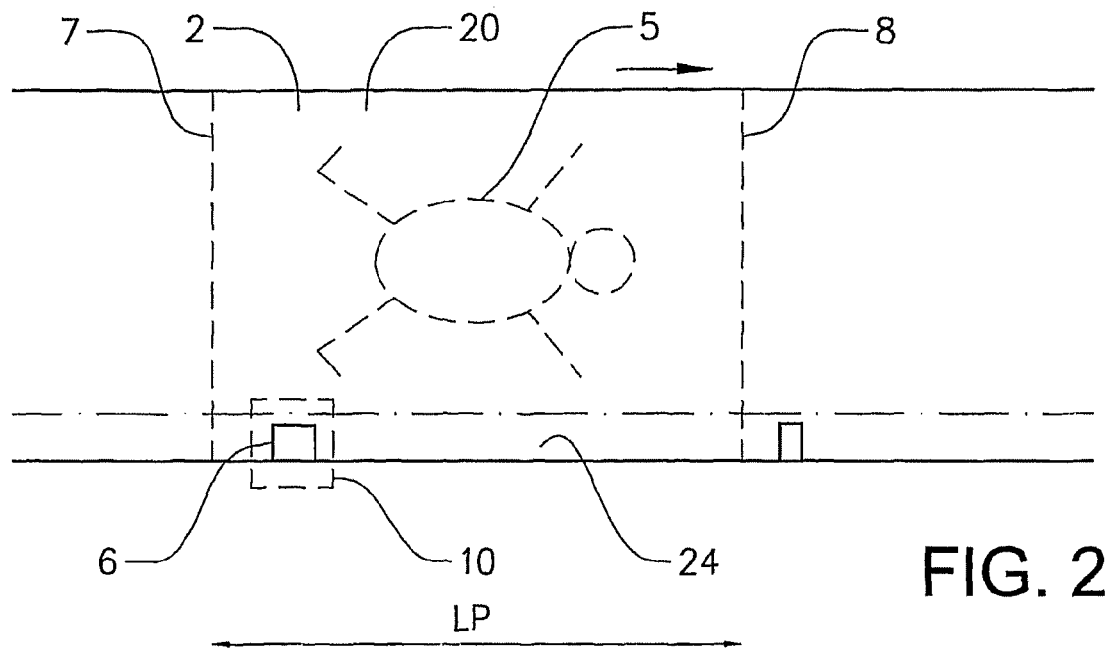
FIG. 2 shows a section of a material web with a synchronizing mark.

FIG. 2 also shows how the detecting device 10 is positioned at a time when the detection of the synchronizing mark 6 occurs, that is when the synchronizing mark 6 is just passing the detecting device 10. The detecting device 10 is suitably arranged with a detecting area that corresponds to a certain section in the form of a line or zone 24 in the machine direction and that goes from the edge of the material web 2 inwards towards its centre. According to the embodiment, the synchronizing mark 6 is preferably positioned with its full extent within this zone 24. The boundary of this zone 24 is indicated in FIG. 2 by a dash dotted line.

An underlying principle behind the invention is that the synchronizing mark 6 is printed on the first material web 2 in a colour or colour combination that can be detected by means of the detecting device 10. More specifically, a detecting device 10 is utilized that is arranged to distinguish between different colours, for example red, green and blue, or in principle between any colours. Such detecting devices 10, and the theory concerning how different colours can be detected, are already known and will therefore not be described here in detail. However, it can be mentioned that an accepted model for colour detection is based on the fact that a certain given colour or tint can be defined by means of a coordinate system with a y-axis that represents the lightness, from L=0 (black) to L=100 (white). In addition, the x-axis represents a colour scale between red (positive values along the x-axis) and green (negative values along the x-axis). An additional axis that also passes through the origin of the coordinate system represents a colour scale between yellow (positive values) and blue (negative values). The method is called in general the CIELab method and can be used to distinguish between all possible tints by the selection of coordinates according to the above principles. The method is also suitable for use with the present invention. The detecting device 10 can thus suitably be arranged to distinguish between different tints by utilizing the following formula:

$$\Delta E_{ab}{}^* = \sqrt{[(\Delta L^*)^2 + (\Delta a^*)^2 + (\Delta b^*)^2]}$$

where the parameter $\Delta E_{ab}{}^*$ can be calculated as described above by using the values of $\Delta L^*$, $\Delta a^*$ and $\Delta b^*$, which then represent differences in the coordinate positions between different tints. The formula above is comprised in an international standard for colour detection, ISO 5631. The theory according to this standard can thus be utilized in such a way that the relevant synchronizing mark 6 can be given a colour with a predefined value of $\Delta E_{ab}{}^*$ as above. A synchronizing mark 6 that, for example, consists of a red line (with a certain predetermined value of $\Delta E_{ab}{}^*$) can thus be detected by a detecting device 10 arranged to detect red objects. When the detecting device 10 detects a tint in its detecting area with a certain predetermined deviation from said predetermined value, this is interpreted as there being no synchronizing marks present at the detection. In this way, a synchronizing mark 6 is detected by distinguishing its colour or colour combination from colours or colour combinations elsewhere along the section 24 where detection can be carried out.

Figure 3:
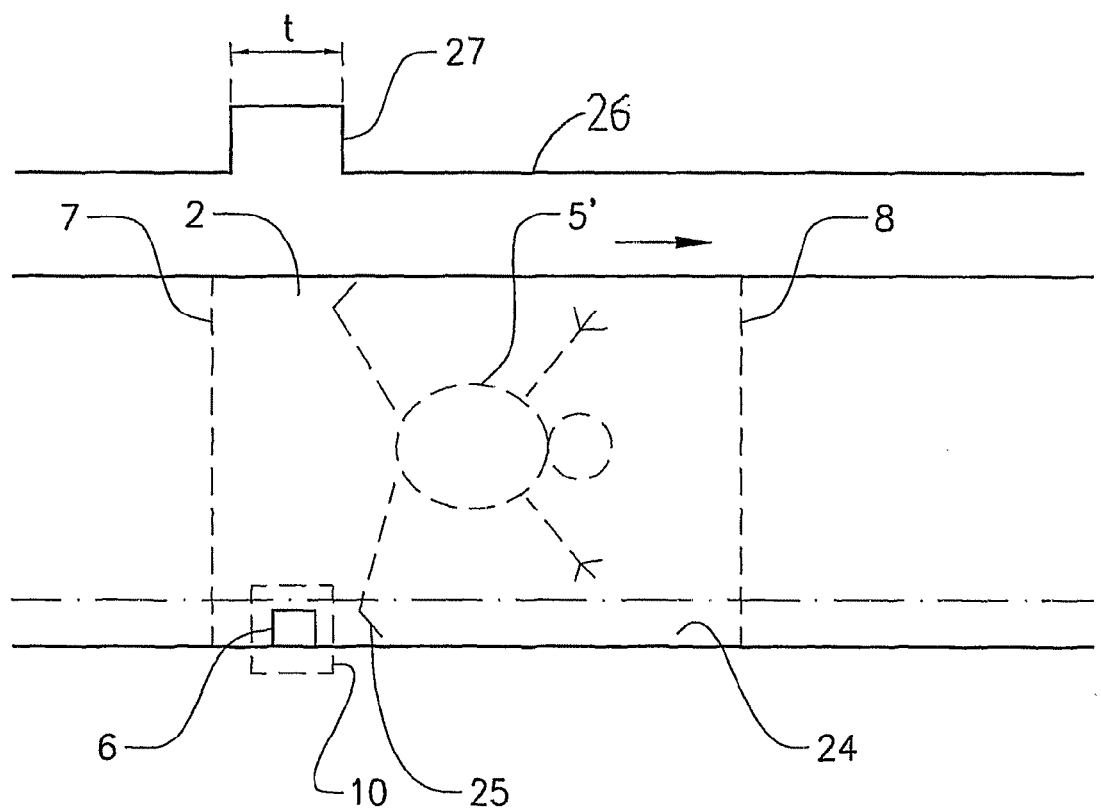
FIG. 3 shows an additional embodiment with a material web and a synchronizing mark.

According to a particular aspect, the synchronizing mark 6 is printed in a colour or colour composition that is different from any section of the printed motif that can be found along the zone 24. This is illustrated in FIG. 3, which shows an alternative embodiment with a printed motif 5' that is modified slightly in relation to what is shown in FIG. 2. Components in FIG. 3 that are the same as corresponding components in FIG. 2 are given the same reference numeral. More specifically, FIG. 3 shows a printed motif 5' in the form of a stick man with a leg 25 that extend into the zone 24, that is within the area that is read by the detecting device 10. If the leg 25 on the stick man 5' is printed in a colour or colour composition that differs from the specific colour in which the synchronizing mark 6 is printed, then, the detecting device 10 will be able to distinguish between the synchronizing mark 6 and the leg 25. In this way, the printed motif 5' is enable to utilize in principle the whole width of the first material web 2. The synchronizing mark 6 can still be distinguished and detected by the detecting device 10, even at relatively high process speeds. A precondition is that the parts of the printed motif 5' that are found in the zone 24 do not have a colour or other optical characteristics that are the same as corresponding characteristics that the detecting device 10 is arranged to detect.

The synchronizing mark 6 is designed in a way and with optical characteristics, suitably concerning its colour or colour combination, that differs from the design of any parts of a printed motif that is found in the zone 24. It should be noted that the invention is not limited to the type of distinguishing that is based only on colour. As an alternative to colour detection, the invention can be realized by detection that is based on other optical characteristics, such as, for example, shape and contrast. For example, the synchronizing mark can be designed with a level of contrast that differs essentially from the level of contrast that is to be found in any section of the printed motif that is to be found in the zone 24.

According to yet another aspect, different combinations of colours and/or optically-based parameters, such as, for example, shape and contrast, can be used for the detection of the synchronizing mark. For example, an alternative synchronizing mark (not shown in the figures) can consist of two or more consecutive lines, instead of only one line as shown in FIG. 3. In the case when two lines are used, these can be printed in two separate colours, for example red and green. The detecting device and the control unit that are used can then be arranged so that a synchronizing mark is detected if and only if there is a detection of a red line followed by a green line. In such an embodiment, a detecting device is suitably used with two separate detectors, one for each colour (red and green respectively). This makes it easier to print motifs in different colours. For example, the parts of the motif that come within the zone 24 can easily be partly red and green. The precondition for this embodiment is, however, that any red and green sections in the motif are not positioned in such a way that they could be perceived by the detecting device as a red line that is followed by a green line. According to this embodiment, a synchronizing mark is thus used that in turn can be said to comprise two or more elements which are arranged as a predetermined combination of optical characteristics. This combination can then be detected by the detecting device. As a result of the colour combination in question not being found elsewhere in the zone 24, the synchronizing mark 6 can be detected in a reliable way.

In addition, increased accuracy in the detection of the synchronizing mark 6 can be achieved if the control unit 13 and the detecting device 10 are arranged in such a way that detection is only carried out for a limited period of time during a division length $L_N$. This is shown schematically in FIG. 3 by a line 26 that comprises a "pulse"-like section 27. This section 27 corresponds to a particular time slot, that is a period of time when it is possible to carry out detection with the detecting device 10. During the remaining parts of the division length $L_N$, no such detection is possible. The time slot corresponds to a short period of time t that occurs when the synchronizing mark 6 is expected to pass the detecting device 10. The advantage of such an embodiment is that the printed motif 5' can, in principle, have any colours at all in the areas that are outside the section 27, even if the printed motif 5' is located completely or partially within the zone 24.

With a normal application for the manufacture of babies' diapers with the arrangement according to the disclosure, the synchronizing mark 6 has preferably a length (that is in the longitudinal direction of the material web 2) that is of the order of 15 mm or more. The width of the synchronizing mark 6 (that is in the transverse direction of the material web 2) is preferably of the order of 25 mm.

An object of the arrangement according to FIG. 1 is to synchronize the first material web 2 with its printed motif 5 in a correct way, so that the printed motif 5 is always positioned in a correct position on each finished product 20. In order to achieve this, the control unit 13 is preferably arranged with a virtual, data-based reference function or "master" function, which will now be described with reference initially to FIG. 4a.

Figure 4A:
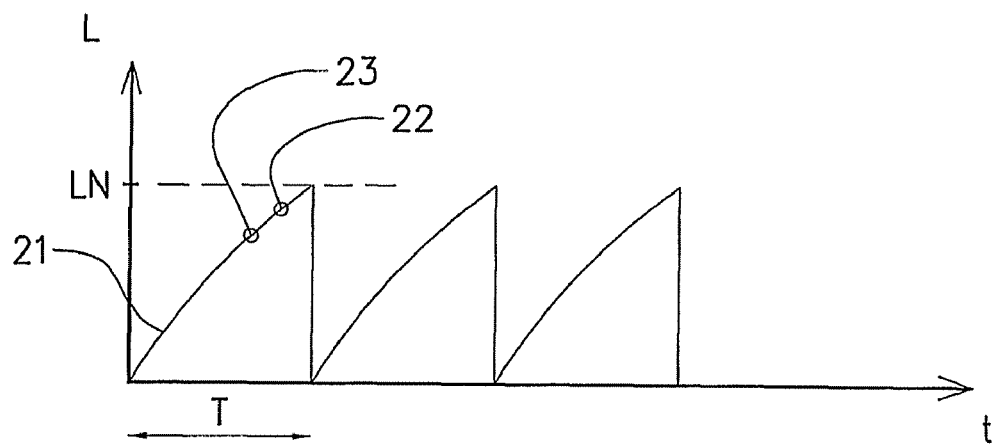
FIG. 4 is a diagram that shows a regulating function in accordance with the invention.

The virtual master function is a cyclic clock that preferably turns one revolution per product 20. As is described in detail below, the master function is not limited just to this periodicity. An event-controlled reading off of this clock can be interpreted as the relative position of the event in question in relation to a fixed point on the product in question, that is in relation to a type of virtual zero point or reference for the product. FIG. 4a shows the virtual master function in the form of a ramp-like curve 21 that recurs at regular intervals.

According to the embodiment, the detecting device 10 is utilized first to detect a particular synchronizing mark 6 along the first material web 2, according to the principles that were described above. When a synchronizing mark 6 is found, the control unit 13 is utilized to detect in what position along the virtual master function 21 the synchronizing mark 6 is located. Information about the actual position of the virtual master function 21 is thus recorded by means of the control unit 13. Thereafter, the control unit 13 compares the actual position of the virtual master function (actual value) with an expected position (desired value). The speed $v_1$ of the first material web 2 is then changed in relation to the speed $v_2$ of the suction conveyor 11 in response to any deviation between the actual position and expected position (that is the desired value). The lower the speed $v_1$ in comparison with $v_2$, the more the material of the first material web 2 will be stretched. This is then utilized to obtain a correct synchronization of the first material web 2.

FIG. 4a shows said reference function in the form of a ramp-like curve 21 that recurs at regular intervals that symbolizes a periodic clock that is utilized for detecting the respective synchronizing mark 6. For this reason, the curve 21 is drawn in an xy-coordinate system where the x-axis corresponds to the time t, and where a period in the curve 21 corresponds to the time T that it takes for a nominal division length $L_N$ of the material in question to pass the detecting device 10. In addition, the y-axis corresponds to a length L for the first material web 2, with a maximal value $L_N$ of the curve 21 corresponding to the length of the respective product. The curve 21 indicates in a schematic way a rise from a zero value that indicates one end of a product to a maximal value $L_N$ that indicates the other end of the product and that, according to the described embodiment, corresponds to the length of the product.

According to the embodiment, a value of the position of the virtual master function that has been read off (when a synchronizing mark 6 has just been detected) is thus compared periodically with an expected position along the virtual master function. The expected value, that is the desired value, is indicated in FIG. 4a by the reference numeral 22 and corresponds to the printed motif 5 being positioned correctly in its intended place on the finished product. The precise position for this desired value 22 is determined by a number of factors, such as, for example, the equipment comprised in the arrangement 1, the dimensions of the comprised material, the process speed, etc. The curve 21 with its desired value 22 thus consists of predefined data that is stored in the control unit 13. For this reason, the reference function or master function that is illustrated by the curve 21 can be said to be "virtual", as it is thus generated and stored in the form of software in the control unit 13.

Figure 4B:
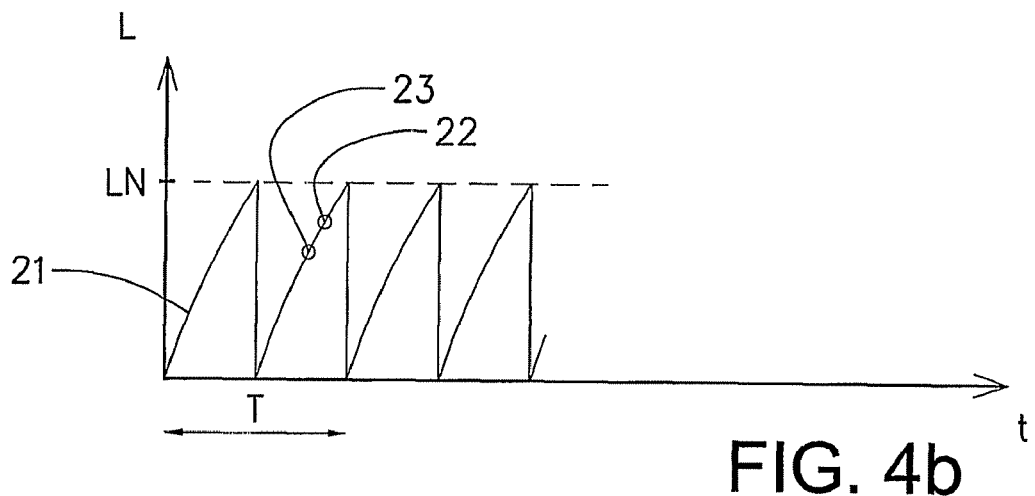
Figure 4C:
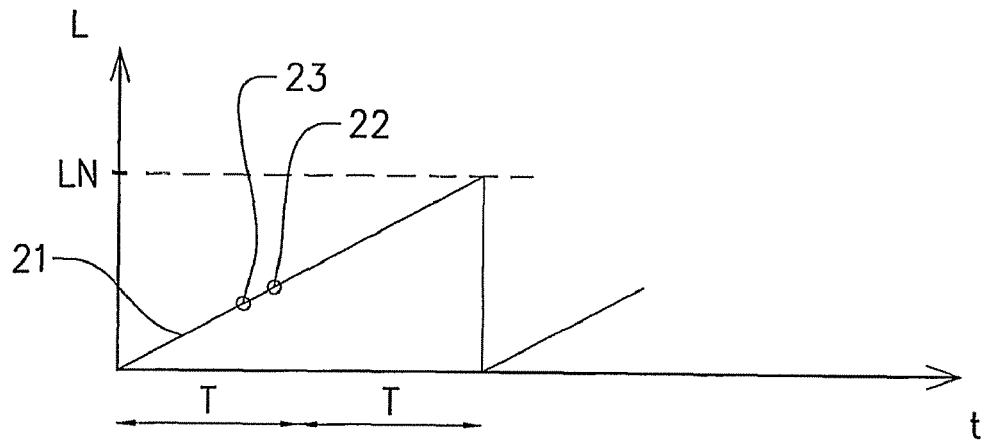

FIG. 4b shows an alternative embodiment, in which the virtual master function 21 is arranged in such a way that two periods in the curve 21 correspond to the time T that it takes for a nominal division length $L_N$ of the material in question to pass the detecting device 10. FIG. 4c shows yet another embodiment of the invention in which the virtual master function 21 is arranged in such a way that a period in the curve 21 corresponds to twice the time T that it takes for a nominal division length $L_N$ of the material in question to pass the detecting device 10.

Taken as a whole, as illustrated by FIGS. 4a, 4b and 4c, the invention can be realized in such a way that the master function 21 consists of a cyclic clock where the number of cycles T per product 20, or alternatively the number of products 20 per cycle T, consists of a whole number. In all the embodiments that are shown in FIGS. 4a, 4b and 4c, the principle is used that detection of a given synchronizing mark 6 is carried out using the detecting device 10. This results in the recording of a position along the curve 21 that corresponds to this detected synchronizing mark 6. This position then constitutes an actual value that is indicated schematically by the reference numeral 23 in FIGS. 4a, 4b, 4c. As the length of the period T for the curve 21 can be said to have a given relationship to the product length of the respective product, the actual value 23 will consist of a numerical value corresponding to a certain proportion of the total product length.

In addition, the control unit 13 is arranged to compare the desired value 22 and the actual value 23 (that is the actual position) that was recorded during the detection of a particular synchronizing mark 6. According to the example that is shown in FIGS. 4a, 4b and 4c, there is a difference between the desired value 22 and the actual value 23. This difference can be expressed as a difference between the proportion of the whole product length that corresponds to the desired value 22 minus the proportion of the product length that corresponds to the actual value 23. If there is a relatively large difference between the desired value 22 and the actual value 23 (as shown in, for example, FIG. 4a), the printed motif 5 would be positioned on the first material web 2 displaced somewhat in relation to its intended position, that is the motif 5 would not then be correctly synchronized. For this reason, the arrangement is arranged in such way that the position of the printed motif 5 on the finished product 20 is adjusted by stretching the first material web 2 if there is such a deviation between the desired value 22 and the measured value 23. For this reason, the synchronizing marks 6 are pre-printed on the first material web 2 in such a way that its periodicity $L_S$ is somewhat shorter than the intended product length $L_N$. This means that the distance $L_S$ between two consecutive synchronizing marks 6 is shorter than the product length $L_N$, which in turn corresponds to the intended final length of the finished product 20. The fact that the distance $L_S$ between two synchronizing marks 6 is shorter than the product length $L_N$ makes it possible to stretch the first material web 2 to a certain extent, in order in this way to position the printed motif 5 so that, in its final position, it is in the correct position on the finished product 20.

According to the embodiment shown, the abovementioned stretching of the first material web 2 is achieved by a regulation of the speed of the first speed-regulating device 14, which in turn controls the feed speed $v_1$ for the first material web 2. More specifically, the control unit 13 is arranged to control the speed-regulating device 14 in such a way that the first material web 2 is given a speed $v_1$ that is somewhat lower than the speed $v_2$ of the suction conveyor 11. This leads in turn to a stretching of the material in the first material web 2 when it runs through the processing equipment 9. In this way, the position of the printed motif 5 on the finished product and thereby also the position of the respective synchronizing mark 6, is adjusted in such a way that the deviation between the desired value 22 and the actual value 23 relating to the position of the synchronizing mark 6 is eliminated.

According to the embodiment, the distance $L_s$ between two consecutive synchronizing marks 6 is of the order of 2% shorter than the product length $L_N$. This makes it possible to utilize the natural elasticity of the first material web 2 for stretching it in accordance with the abovementioned principles. The ratio between the product length $L_N$ and the distance between two synchronizing marks $L_S$ can, however, vary depending upon the comprised material and which type of processing equipment is utilized. Nor is the invention limited to the nominal division length having to be connected to the product length, but instead other divisions of first material web 2 are also possible.

To sum up, the arrangement that is described is used for the detection of synchronizing marks 6, the position of which is detected and utilized for synchronizing a printed motif 5 in the correct intended position on a finished product. The detection of the respective synchronizing mark 6 is carried out as described above, by utilizing a colour or colour composition that is distinct from any sections of a printed motif that may be found along the zone 24 (see FIG. 3). The actual synchronization is carried out using a virtual reference function or "master" function that is stored in the control unit 13 and that is arranged to provide references in order to make it possible to stretch the first material web 2 if a deviation is recorded between an actual position and the expected position of the respective synchronizing mark 6. In this way, a simple and accurate process is obtained for synchronizing the printed motif 5.

The invention is not limited to what is described above, various embodiments being possible within the framework of the patent claims. For example, the invention is particularly suitable for use in association with a manufacturing process for making absorbent products such as diapers, incontinence protectors, sanitary towels and panty liners, but, however, is not limited only to this type of product, being able, in principle, to be utilized in other manufacturing processes that are based on an essentially continuous material web being divided into a certain product length and where a printed motif or other similar process is synchronized in the correct position.

In addition, it can be pointed out that, when required, the respective synchronizing mark can be positioned in a position that is intended to be cut away from the product after the synchronizing mark has been detected. Similarly, the respective synchronizing mark can be arranged so that it is concealed by, for example, the tapes that are applied after the detection has been carried out.

The invention is particularly suitable for use with the applications where the first material web 2 consists of a material intended to form a backing layer in a diaper. Such a material then consists suitably of a plastic film that is non-permeable to liquid, which is suitable for the abovementioned stretching procedure and is also suitable for printing with high quality colour motifs. The invention can, however, be used with other material than just the backing layer for diapers, for example other elastic and stretchable material webs, for example non-woven material, that is fibrous materials with fibres such as for example polyolefins, that is polymer material such as polyethylene and polypropylene, or alternatively polyester, nylon or the like. The invention can also be utilized when the first material web consists of some other type of synthetic or textile material. The invention can also be used for different types of laminated product comprising varying numbers of layers of material.

Regarding the printed motif 5, this can be provided by being pre-printed onto the first material web 2. Alternatively, the actual manufacturing process that is obtained with the processing equipment 9 can comprise a process for printing the motif.

In addition, it can be noted, with reference to FIGS. 4a, 4b and 4c, that a period length T in the reference function 21 can correspond to a product length, as described above. Alternatively, a period length T can correspond to two or more product lengths, or a certain proportion of a product length. This means that the synchronizing marks can be positioned in a corresponding way, for example in every other position in comparison with what is shown in FIG. 1.

With reference to FIGS. 4a, 4b and 4c, it can be pointed out that the invention is not limited to a virtual master function where a period corresponds clearly to a product length. Alternatively, the invention can be arranged in such a way that a given product length corresponds to two or more synchronizing marks and thus also two or more periods in the virtual master function.

The invention claimed is:

1. A method for detection of a synchronizing mark being used in synchronized positioning of at least one essentially continuous material web, for manufacturing products that comprise a printed motif, which material web is intended to be divided into a nominal division length and comprises synchronizing marks with a periodicity, which method comprises:
    establishing a longitudinal detection zone along a side edge of the material web, said longitudinal detection zone including the printed motif and the synchronizing mark;
    detection of a respective synchronizing mark for positioning a respective motif in a predetermined position on the respective product, which detection is carried out in said longitudinal detection zone in a machine direction of said material web; and
    detection of said synchronizing mark by distinguishing its optical characteristics from optical characteristics of the printed motif.

2. The method according to claim 1, wherein the method comprises detection of said synchronizing mark by distinguishing its colour from colours in the the printed motif.

3. The method according to claim 1, wherein the method comprises detection of said synchronizing mark by distinguishing its colour combination from colours and colour combinations in the printed motif.

4. The method according to claim 1, wherein said detection comprises distinguishing of optical characteristics in the form of shape, contrast or characteristics of the synchronizing mark.

5. The method according to claim 1, wherein said detection is carried out by a detecting device arranged to detect predetermined colours or colour combinations.

6. The method according to claim 1, wherein said synchronizing mark comprises two or more elements which are arranged as a predetermined combination, arranged to be detected by said detecting device.

7. The method according to claim 1, wherein the nominal division length consists of a predetermined product length for said product.

8. The method according to claim 1, wherein said product consists of an absorbent product and in the method comprises the provision of a material web in the form of a layer for such an absorbent product.

9. The method according to claim 8, wherein the material web consists of a backing layer for said product.

10. A method for manufacturing absorbent products using at least one essentially continuous material web, which said products comprise a printed motif, with said material web being intended to be divided into a nominal division length and comprising synchronizing marks with a periodicity, which method comprises:

feeding said material web into a processing equipment;

processing in said processing equipment with various process steps for said manufacture; and detection of the respective synchronizing mark for positioning a respective printed motif in a predetermined position, which detection is carried out in predetermined section a machine direction of said material web;

positioning said motif in a longitudinal detection zone along a side edge of the material web, said longitudinal zone including the printed motif and the synchronizing mark; and creating said synchronizing mark with an optical characteristic that is arranged to be able to be distinguished from an optical characteristic of said motif that are placed within said longitudinal detection zone.

11. The method according to claim 10, wherein the material web consists of a side panel, a top layer, wadding material or similar material component in said product.

12. The method according to claim 10, wherein the material web consists of a side panel in said product.

13. An arrangement for detecting a synchronizing mark for synchronized positioning of at least one essentially continuous material web for manufacturing products that comprise a printed motif, which material web is adapted to be divided into a nominal division length and comprises synchronizing marks with a periodicity, which arrangement comprises a detector for detecting the respective synchronizing mark in a machine direction of said material web, and a computer-based control unit arranged for said synchronization, whereby the motif is positioned in a longitudinal detection zone along a side edge of the material web, said longitudinal detection zone including the printed motif and the synchronizing mark, the control unit is arranged to detect said synchronizing mark by distinguishing its optical characteristics from optical characteristics of the printed motif.

14. An absorbent product such as a diaper, incontinence protector, sanitary towel or panty liner, with a predetermined division length and comprising a backing material that has a processed element in the form of a printed motif, and comprising a synchronizing mark with predetermined periodicity, with said synchronizing mark and said printed motif being arranged in a longitudinal detection zone along a side edge of said backing material, said synchronizing mark is arranged with optical characteristics that can be distinguished from optical characteristics of the printed motif.

15. The absorbent product of claim 14, wherein the absorbent product is a diaper, incontinence protector, sanitary towel, or a panty liner.

* * * * *